United States Patent [19]

Addor et al.

[11] 4,009,279
[45] Feb. 22, 1977

[54] METHODS FOR CONTROLLING INSECTS AND ACARINA

[75] Inventors: Roger Williams Addor; James Byron Lovell, both of Pennington; Sidney Kantor, Trenton, all of N.J.

[73] Assignee: American Cyanamid Company, Stamford, Conn.

[22] Filed: Sept. 25, 1975

[21] Appl. No.: 616,792

Related U.S. Application Data

[62] Division of Ser. No. 493,944, Aug. 14, 1974, Pat. No. 3,928,382, which is a division of Ser. No. 235,397, March 16, 1972, abandoned.

[52] U.S. Cl. .......................... 424/277; 424/DIG. 12
[51] Int. Cl.² .......................................... A01N 9/00

[58] Field of Search ..................... 424/277, DIG. 12

[56] References Cited

UNITED STATES PATENTS

| 3,322,788 | 5/1967 | Gompper | 260/327 |
| 3,484,455 | 12/1969 | Addor | 424/277 |
| 3,489,771 | 1/1970 | Donche | 260/327 |

Primary Examiner—V. D. Turner
Attorney, Agent, or Firm—Harry H. Kline

[57] ABSTRACT

Novel 2-imino-1,3-dithiethanes and the use thereof in controlling insects and acarina are disclosed.

10 Claims, No Drawings

METHODS FOR CONTROLLING INSECTS AND ACARINA

This application is a divisional of our copending application, Ser. No. 493,944, filed on Aug. 14, 1974, now U.S. Pat. No. 3,928,382, issued on Dec. 23, 1975, which in turn is a division of our applicaion, Ser. No. 235,397, filed on Mar. 16, 1972, now abandoned.

This invention relates to novel 2-imino-1,3-dithietanes and to the use thereof in controlling insects and acarina. More particularly, it relates to controlling insects and acarina by contacting the ova of said insects and acarina with an ovicidal amount of said compounds. Further, it relates to their control by applying said compounds to the habitat or dietary medium, such as foliage or vegetation, manure and the like, of said insects and acarina in an amount sufficient to suppress the fecundity of said insects and acarina. It further relates to the control of insects by applying said compounds to the larvae, larval habitat or dietary medium of said larvae in an amount effective to produce the juvenile hormone effect therein. It further relates to controlling insects and acarina by applying a larvicidally effective amount of said compounds to the larvae, larval habitat or dietary media of said larvae. It further relates to a method for controlling Ixodides by applying a chemosterilizing amount of said compounds to the adult female ixodid ticks.

The novel 2-imino-1,3-dithietanes have the structures depicted as formulas I to VI below:

(I) 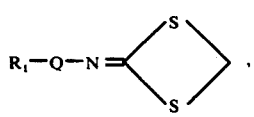

(II) 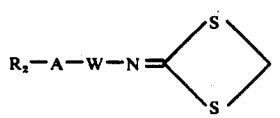

(III) 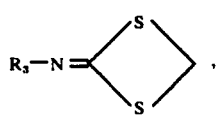

(IV) 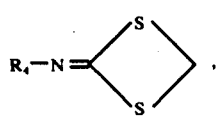

(V) 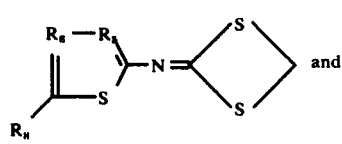 and (VI) 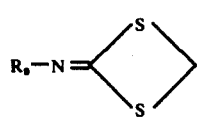

Novel 2-aralkyl and 2-heterocyclicalkylimino-1,3-dithietanes have the formula (I) structure:

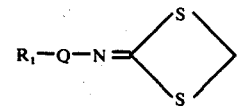

wherein Q represents a member selected from the group consisting of alkylene and alkyl substituted alkylene having a total of 1 to 4 carbon atoms; $R_1$ represents a member selected from the group consisting of

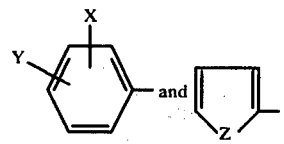

or when $R_1$-Q are taken together they may represent

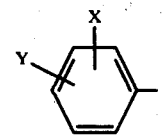

X and Y each represent a member selected from the group consisting of hydrogen, halogen and alkyl $C_1$–$C_4$ or when X and Y are taken together on adjacent carbons they may form a benzo group; Z represents a member selected from the group consisting of oxygen, sulfur and NH; and with the proviso that when Q is methylene and $R_1$ is

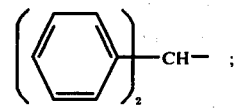

then X and Y cannot both be hydrogen, nor can one of X and Y be hydrogen and the other halogen.

Novel formula (II) compounds have the structure:

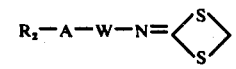

wherein W represents a member selected from the group consisting of methylene, ethylene and loweralkyl $C_1$–$C_5$ substituted methylene and ethylene; A represents a member selected from the group consisting of sulfur and oxygen; $R_2$ represents a member selected from the group consisting of alkyl $C_1$–$C_{12}$ including straight and branched chain alkyl, cyclic alkyl and bicyclic alkyl, phenyl, mono and diloweralkyl ($C_1$–$C_4$) phenyl, mono and dihalophenyl, furfuryl, tetrahydrofurfuryl, alkenyl $C_2$–$C_8$, and loweralkoxy ($C_1$–$C_4$) lower alkyl ($C_2$–$C_3$).

Novel formula (III) compounds have the structure:

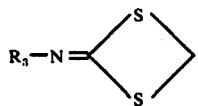

wherein $R_3$ represents a member selected from the group consisting of benzene sulfonyl, diloweralkylcarbamoyl $C_2$-$C_9$, diloweralkylthiocarbamoyl $C_2$-$C_9$, loweralkoxycarbonyl $C_2$-$C_5$, and ar-(loweralkyl)oxycarbonyl $C_8$-$C_{16}$.

The novel compounds of formula (IV) have the structure.

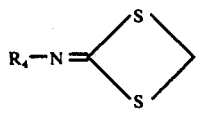

wherein $R_4$ represents a member selected from the group consisting of pyridyl, mono or diloweralkyl substituted pyridyl, nitro substituted pyridyl, and mono or dihalo substituted pyridyl.

Novel formula (V) compounds have the formula:

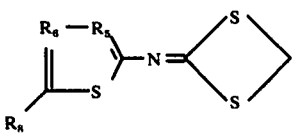

wherein $R_5$ and $R_6$ each represent a member selected from the group consisting of N and $CR_7$; and, $R_7$ and $R_8$ each represent a member selected from the group consisting of hydrogen and loweralkyl $C_1$-$C_4$.

The novel compounds of formula (VI) have the structure:

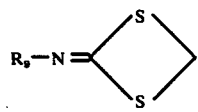

wherein $R_9$ represents a member selected from the group consisting of alkyl $C_6$-$C_{12}$ and alkenyl $C_3$-$C_{12}$.

As used herein, the expression halo includes fluoro, chloro, bromo and iodo.

The compounds of this invention can be synthesized by reacting the appropriate alkali metal or ammonium dithiocarbamate salt with a methylene halide such as methylene iodide or methylene bromide. The reaction is generally carried out in the presence of (1) a base such as an alkali metal hydroxide, carbonate or bicarbonate, a tertiary amine or other weak base and (2) an inert organic solvent such as dimethylformamide. Preferably, this reaction is carried out at a relatively low temperature, for example between about 20° C. and 50° C.

The dithiocarbamate salt can be prepared by reacting the appropriate amine with carbon disulfide and base or it can be synthesized from the appropriately substituted isothiocyanate by reaction with alkali metal hydrosulfide in a suitable solvent.

When the compounds of this invention are utilized as control agents for insects and acarina, such compounds may be brought into contact with the adult females of said pests or they may be applied to the habitat, breeding grounds and/or dietary media, such as vegetation, foliage, manure, and the like, of said pests. The application is preferably made at a dosage concentration which is sublethal for adult insects and acarina, but which level provides ultimate control of said pests through ovicidal or larvicidal activity or by suppression of fecundity, inhibition of metamorphosis, juvenile hormone effect or chemosterilization of said pests.

In practice, the active compounds will generally be formulated with conventional solid or liquid agricultural adjuvants or formulation aids and applied by conventional means. They may be formulated as dusts, dust concentrates, wettable powders, emulsifiable concentrates or the like. They may also be incorporated in baits upon which insects and acarina feed.

Wettable powders and emulsifiable concentrates are particularly useful since they can be diluted with water and applied as dilute liquid sprays to the foliage, stems and other parts of plants for which protection is sought or they may be applied topically to animals which are to be protected from attack. In the latter situation the dilute liquid formulations may be used as dips as well as sprays.

Dusts or dust concentrates, can be prepared by grinding together the inert solid diluent such as attapulgite, kaolin, walnut shell flour, diatomaceous earth, ground corn cob grits, or ground cocoanut shell, and the active ingredient, where such active ingredient is in solid form. Where the active ingredient is liquid, it may be sprayed on the carrier and thoroughly mixed with it or it may be dissolved in a solvent such as acetone or xylene, and the solution sprayed on the solid carrier. Dusts usually contain from about 1% to 15% by weight of active ingredient, whereas concentrates may contain from about 16% to about 85% by weight of the active material.

Wettable powders are prepared in the same fashion as dust concentrates, excepting that about 5% to 10% by weight of a surfactant is also added.

The compounds of the present invention may also be prepared as emulsifiable concentrates by dissolving or dispersing about 10% to 75% by weight of the active compound in a suitable solvent or carrier such as a petroleum distillate having a minimum aromatic content of 85% and admixing therewith about 10% by weight of an emulsifier such as polyoxyethylene derivatives and blends with alkyl aryl sulfonates. These concentrates are also generally dispersed in water or other suitable solvent for application.

As ovicidal agents, we have found that generally about 0.4 ppm. to about 2500 ppm. of the substituted 2-imino-1,3-dithietane is effective for preventing the embryogenesis of insect and acarina ova.

We have also found that control of the larval stages of certain insects requires the application of from about 0.25 pound to 8.0 pounds per acre of the active ingredient. Control of the larval stages of ticks, however, can usually be obtained with the substituted 2-imino-1,3-dithietane in a dilute formulation containing from about 10 ppm. to 2000 ppm., and generally 10 ppm. to 1000 ppm. of the dithietane.

The dithietanes may be used to control Ixodid population by application thereof to Argasid or Ixodid adult female ticks such as *Boophilus, Amblyomma, Anocen-* tor, *Dermacentor, Ixodes, Haemaphysalis, Hyalomma, Rhipicentor, Margarpus, Rhipicephalus, Argas, Otobius,* and *Ornithodons* whereby chemosterilization occurs, i.e., their egg production is inhibited, or if laid, the embryogenesis of the egg is prevented.

Illustrative of the insect larvae in which suppression of fecundity, production of the juvenile hormone effect, including dwarfing or otherwise interfering with normal metamorphosis are: Lepidoptera, such as the southern armyworm (*Prodenia eridania*); Coleoptera, such as the confused flour beetle (*Tribolium confusum*) and Mexican bean beetle (*Epilachna varivestis*), or southern corn rootworm (*Diabrotica undecimpunctata howardi*); and Diptera, such as the mosquito (*Anopheles quadrimaculatus*) and the house fly (*Musca domestica*).

It has also been observed that the pupae of certain insect species which are obtained from larvae reared in a habitat or medium treated with a sublethal concentration of the dithietanes, have no adult insect emergence, or in some instances, produce deformed adults which expire shortly after emergence.

Preparation of and the effectiveness of the compounds employed in the present invention is further demonstrated in the examples below which are not to be taken as being limitative of the present invention. Unless otherwise indicated, all parts and percentages employed herein are by weight.

EXAMPLES 1–8

Preparation of 2-(2-Chlorobenzylimino)-1,3-dithietane

A mixture of 21.2 g. of 2-chlorobenzylamine, 12.6 g. of carbon disulfide, and 6.0 g. of porous sodium hydroxide beads was stirred in 100 ml. of dimethylformamide until the beads had dissolved. This mixture was added dropwise to a mixture of 52.0 g. of methylene bromide and 15.2 g. of triethylamine while keeping the reaction temperature below 35° C. by cooling with an ice bath. After stirring the mixture overnight, it was poured into ice-water and the resulting oil was partitioned into benzene. The benzene mixture, after being washed with dilute alkali and water, was dried and concentrated in vacuo to give 31.0 g. of crude product. The oil was redissolved in methylene chloride and the mixture was saturated with dry hydrogen chloride. The resulting solids were collected, washed with methylene chloride, and then stirred at 40° C. with a benzene-water mixture until the solids disappeared. The benzene layer was separated and dried and, on concentration in vacuo, afforded 16.0 g. of pure product as a light yellow oil.

Anal.: Calc'd. for $C_9H_3ClNS_2$: C, 47.05; H, 3,51; Cl, 15.43; N, 6.10; S, 27.91. Found: C, 47.01; H, 3.39; Cl, 15.74; N, 6.20; S, 28.00.

Following the above procedure but substituting benzylamine, 4-methylbenzylamine, 4-chlorobenzylamine, 3-chlorobenzylamine, 3,4-dimethylbenzylamine, 3,4-dichlorobenzylamine or 2,4-dichlorobenzylamine for 2-chlorobenzylamine, yields respectively:

| Example No. | Compound | m.p. ° C. |
|---|---|---|
| 2 | 2-Benzylimino-1,3-dithietane | oil |
| 3 | 2-(4-Methylbenzylimino)-1,3-dithietane | oil |
| 4 | 2-(4-Chlorobenzylimino)-1,3-dithietane | oil |
| 5 | 2-(3-Chlorobenzylimino)-1,3-dithietane | oil |
| 6 | 2-(3,4-Dimethylbenzylimino)-1,3-dithietane | oil |
| 7 | 2-(3,4-Dichlorobenzylimino)-1,3-dithietane | 71–72 |

-continued

| Example No. | Compound | m.p. ° C. |
|---|---|---|
| 8 | 2-(2,4-Dichlorobenzylimino)-1,3-dithietane | 48–49 |

EXAMPLES 9–11

Preparation of 2-Furfurylimino-1,3-dithietane

A mixture of 13.7 g. of triethylammonium furfuryldithiocarbamate, 10.5 ml. of methylene bromide, and 7.0 ml. of triethylamine in 100 ml. of dimethylformamide was stirred for several hours and then poured into ice-water. The oily product was partitioned into ether and the ether mixture was extracted with 3N hydrochloric acid. After extracting the acidic solution with methylene chloride, it was made basic with potassium hydroxide solution and re-extracted with methylene chloride. The methylene chloride mixture, after water washing, drying, and concentrating in vacuo afforded 4.9 g. of the desired dithietane as a yellow oil.

Anal.: Calc'd. for $C_7H_7NOS_2$: C, 45.38; H, 3.81; N, 7.56. Found: C, 45.84; H, 4.34; N, 7.79.

Following the above procedure but substituting triethylammonium thenyldithiocarbamate or triethylammonium 2-pyrrolylmethyldithiocarbamate for triethylammonium furfuryldithiocarbamate, yields respectively:

| Example No. | Compound | m.p. ° C. |
|---|---|---|
| 10 | 2-Thenylimino-1,3-dithietane | 55–56.5 |
| 11 | 2-(2-Pyrrolylmethylimino)-1,3-dithietane | 100–101 |

EXAMPLES 12–15

Preparation of 2-(Diphenylmethylimino)-1,3-dithietane

Potassium diphenylmethyldithiocarbamate was prepared from diphenylmethyl isothiocyanate and potassium hydrosulfide in a t-butyl alcohol acetone mixture. A mixture of 29.7 g. of this salt, 26.1 g. of methylene bromide, and 10.1 g. of triethylamine in 200 ml. of dimethylformamide was stirred for about one hour keeping the initial reaction temperature below 30° C. by cooling. The mixture was poured into ice-water, partitioned into ethylene chloride, and gave 24.0 g. of crude product upon evaporation of the ethylene chloride. Purification by dry column chromatography on silica gel using 20% methylene chloride in hexane for developing gave 5.5 g. of solids which were recrystallized from isopropyl alcohol to give 4.4 g. of white crystals, m.p. 106.5°–107.5° C.

Anal.: Calc'd. for $C_{15}H_{13}NS_2$: C, 66.41; H, 4.79; N, 5.16; S, 23.64. Found: C, 66.36; H, 4.83; N, 5.17; S, 23.65.

Following the above procedure, and substituting potassium 1-naphthylmethyldithiocarbamate, potassium α-methylbenzyldithiocarbamate or potassium phenethyldithiocarbamate for potassium diphenylmethyldithiocarbamate, yields respectively:

| Example No. | Compound | m.p. ° C. |
|---|---|---|
| 13 | 2-(Naphthylmethylimino)-1,3-dithietane | 47–49 |
| 14 | 2-(α-Methylbenzylimino)-1,3-dithietane | oil |
| 15 | 2-(Phenethylimino)-1,3-dithietane | oil |

EXAMPLES 16–25

Preparation of 2-(p-Chlorophenoxymethylimino)-1,3-dithietane

Potassium p-chlorophenoxymethyldithiocarbamate was prepared by the reaction of p-chlorophenoxymethyl isothiocyanate with potassium hydrosulfide in a mixture of t-butyl alcohol and acetone.

To a mixture of 19.3 g. of methylene bromide and 3.7 g. of triethylamine in 100 ml. of dimethylformamide was added 10.0 g. of potassium p-chlorophenoxymethyldithiocarbamate in portions. After one to two hours, the mixture was poured into water and partitioned into ethylene chloride. The dried ethylene chloride mixture was saturated with dry hydrogen chloride and the resulting salt collected by filtration. Hydrolysis of the salt in a chloroform-water mixture followed by separation, drying and concentration of the chloroform layer gave 3.5 g. of the dithietane as pale yellow crystals, m.p. 64.5°–66.0° C.

Anal.: Calc'd. for $C_9H_8ClNOS_2$: C, 44.00; H, 3.25; N, 5.70. Found: C, 43.78; H, 3.26; N, 5.58.

Following the above procedure, and substituting the appropriately substituted dithiocarbamate salt for potassium p-chlorophenoxymethyldithiocarbamate, yields the following compounds:

| Example No. | Compound | m.p. ° C. |
|---|---|---|
| 17 | 2-(2-Ethoxyethylimino)-1,3-dithietane | oil |
| 18 | 2-(Benzyloxymethylimino)-1,3-dithietane | oil |
| 19 | 2-(Methoxymethylimino)-1,3-dithietane | oil |
| 20 | 2-(Isopropoxymethylimino)-1,3-dithietane | oil |
| 21 | 2-(2-Ethoxyethoxymethylimino)-1,3-dithietane | oil |
| 22 | 2-(Furfuryloxymethylimino)-1,3-dithietane | oil |
| 23 | 2-(Methylallyloxymethylimino)-1,3-dithietane | oil |
| 24 | 2-(2-Bornyloxymethylimino)-1,3-dithietane | oil |
| 25 | 2-(4-Chloro-o-tolyloxymethylimino)-1,3-dithietane | 58–60 |

EXAMPLES 26–35

Preparation of 2-(Phenylthiomethylimino)-1,3-dithietane

Potassium phenylthiomethyldithiocarbamate was prepared by the reaction of phenylthiomethyl isothiocyanate and potassium hydrosulfide in a t-butyl alcohol acetone mixture.

To a mixture of 28.2 g. of methylene bromide and 10.9 g. of triethylamine in 250 ml. of dimethylformamide was added, in portions, 27.3 g. of potassium phenylthiomethyldithiocarbamate keeping the reaction temperature below 30° C. by cooling. After another two hours, the mixture was poured into water and extracted with ethylene chloride. The ethylene chloride mixture was washed with water, dried, and saturated with dry hydrogen chloride. The resulting salt was collected by filtration and washed with acetone. The salt, on stirring with a mixture of 100 ml. of water and 300 ml. of chloroform, dissolved and removal and concentration of the chloroform layer gave 8.5 g. of the dithietane as a white solid, m.p. 50–52° C.

Anal.: Calc'd. for $C_9H_9NS_3$: C, 47.56; H, 3.96; N, 6.16; S, 42.31. Found: C, 47.76; H, 3.88; N, 6.17; S, 42.02.

Following the above procedure, and substituting the appropriately substituted dithiocarbamate salt for potassium phenylthiomethyldithiocarbamate, yields the followin compounds:

| Example No. | Compound | m.p. ° C. |
|---|---|---|
| 27 | 2-(Methylthiomethylimino)-1,3-dithietane | oil |
| 28 | 2-(p-Chlorophenylthiomethylimino)-1,3-dithietane | 101–103 |
| 29 | 2-(tert-Butylthiomethylimino)-1,3-dithietane | oil |
| 30 | 2-(p-Chlorobenzylthiomethylimino)-1,3-dithietane | liquid |
| 31 | 2-(Methoxycarbonylmethylthiomethylimino)-1,3-dithietane | liquid |
| 32 | 2-(m-Tolylthiomethylimino)-1,3-dithietane | liquid |
| 33 | 2-(Furfurylthiomethylimino-1,3-dithietane | liquid |
| 34 | 2-(Isopropylthiomethylimino)-1,3-dithietane | liquid |
| 35 | 2-(Hexylthiomethylimino)-1,3-dithietane | liquid |
| 35-A | 2-(2-Ethylthioethylimino)-1,3-dithietane | liquid |

EXAMPLES 36–49

Preparation of 2-Isopropyloxycarbonylimino-1,3-dithietane

To a well-stirred mixture of 2.8 g. of 2-imino-1,3-dithietane hydrochloride and 24.5 g. of isopropyl chloroformate was added 3.3 g. of powdered sodium acetate in small portions. After stirring for about one hour, the mixture was diluted with 50 ml. of benzene and stirred another hour. An ice-water mixture was added and mixing continued for 2 hours. The benzene phase was separated and the water extracted with fresh benzene. After combining and drying the benzene extracts, evaporation left 5.4 g. of off-white crude product. Recrystalllization from hexane afforded 2.5 g. of white solid, m.p. 72.0°–73.0° C.

Anal.: Calc'd. for $C_6H_9NO_2S_2$: C, 37.68; H, 4.74; N, 7.32; S, 33.53. Found: C, 37.47; H, 4.82; N, 7.57; S, 33.47.

Following the above procedure, but substituting the appropriate diloweralkylcarbamoyl chloride, diloweralkylthiocarbamoyl chloride, loweralkoxycarbamoyl chloride, ar-(loweralkyl) oxycarbonyl chloride or benzene sulfonyl chloride for isopropyl chloroformate, yields the following compounds:

| Example No. | Compound | m.p. ° C. |
|---|---|---|
| 37 | 2-(N,N-Dipropylthiocarbamoylimino)-1,3-dithietane | |
| 38 | 2-(Methoxycarbonylimino)-1,3-dithietane | 82–83 |
| 39 | 2-(Phenylsulfonylimino)-1,3-dithietane | 119.8–121.2 |
| 40 | 2-(N,N-Dimethylthiocarbamoylimino)-1,3-dithietane | 92–93.5 |
| 41 | 2-(Ethoxycarbonylimino)-1,3-dithietane | 57.5–59 |
| 42 | 2-(N,N-Diethylthiocarbamoylimino)-1,3-dithietane | oil |
| 43 | 2-(N,N-Dibutylcarbamoylimino)-1,3-dithietane | oil |

-continued

| Example No. | Compound | m.p. ° C. |
|---|---|---|
| 44 | 2-(N,N-Diethylcarbamoylimino)-1,3-dithietane | oil |
| 45 | 2-(N,N-Dimethylcarbamoylimino)-1,3-dithietane | 74–75.5 |
| 46 | 2-(Benzyloxycarbonylimino)-1,3-dithietane | oil |
| 47 | 2-(1-Methylheptyloxycarbonylimino)-1,3-dithietane | oil |
| 48 | 2-(1-Methylpropyloxycarbonylimino)-1,3-dithietane | oil |
| 49 | 2-(N-Ethylthiocarbamoylimino)-1,3-dithietane | |

EXAMPLES 50–60

Preparation of 2-(2-Pyridylimino)-1,3-dithietane

Triethylammonium 2-pyridyldithiocarbamate (27.1 g.) was dissolved in 100 ml. of dimethylformamide and added dropwise to a stirred mixture of 14 ml. of triethylamine and 36.3 ml. of methylene bromide in 65 ml. of dimethylformamide. After addition was complete, the mixture was stirred another 1.5 hr. and then poured into water. The resulting mixture was extracted with ether and, after being washed with water, the ether mixture was extracted with several portions of 3N sulfuric acid. The aqueous extract was cooled in an ice bath and then made alkaline with 8N sodium hydroxide. The product was collected by filtration and washed with water. The crude dry product (12.0 g.) was recrystallized from ethanol to give 10.1 g. of colorless solid, m.p. 98.7°–99.7° C.

Anal.: Calc'd. for $C_7H_6N_2S_2$: C, 46.13; H, 3.32; N, 15.37; S, 35.18. Found: C, 45.95; H, 3.31; N, 15.13; S, 35.12.

Following the procedure above, but substituting the appropriately substituted pyridyldithiocarbamate salt for triethylammonium 2-pyridyldithiocarbamate, yields the following compounds:

| Example No. | Compound | m.p. ° C. |
|---|---|---|
| 51 | 2-(3-Pyridylimino)-1,3-dithietane | 76–77 |
| 52 | 2-(4-Pyridylimino)-1,3-dithietane | 137.5–139.5 |
| 53 | 2-(5-Chloro-2-pyridylimino)-1,3-dithietane | 166–168 |
| 54 | 2-(4-Methyl-2-pyridylimino)-1,3-dithietane | 102–103.5 |
| 55 | 2-(3-Methyl-2-pyridylimino)-1,3-dithietane | 80–81 |
| 56 | 2-(6-Methyl-2-pyridylimino)-1,3-dithietane | oil |
| 57 | 2-(4,6-Dimethyl-2-pyridylimino)-1,3-dithietane | 92.5–93 |
| 58 | 2-(5-Bromo-2-pyridylimino)-1,3-dithietane | 159–161 |
| 59 | 2-(5-Nitro-2-pyridylimino)-1,3-dithietane | 195–196 |
| 60 | 2-(5-Methyl-2-pyridylimino)-1,3-dithietane | 100–103 |

EXAMPLES 61–65

Preparation of 2-(2-Thiazolyl)imino-1,3-dithietane

Triethylammonium 2-thiazolyldithiocarbamate was prepared by the method of E. B. Knott. This salt (27.7 g.) in 100 ml. of dimethylformamide was added dropwise to a stirred mixture of 14.0 ml. of triethylamine and 36.3 ml. of methylene bromide in 65 ml. of dimethylformamide. After addition was complete, the reaction mixture was stirred for 1.5 hours and poured into 600 ml. of water. The resulting mixture was extracted with ether. The ether was washed with water and then extracted with several portions of 3N sulfuric acid. Some crystals which formed in the acid extract were collected and shown to be the same as the solid product obtained by making the acid extract basic with 8N sodium hydroxide. The combined recovered solids were recrystallized from methanol to give 12.2 g. of gold needles, m.p. 114.5°–116.5° C. Further filtering through silical gel, stirring the filtrate with activated charcoal, recovering the product by evaporation, and recrystallizing from methanol afforded 10.0 g. of white solid, m.p. 116.5°–117.5° C.

Anal.: Calc'd. for $C_5H_4N_2S_3$: C, 31.90; H, 2.14; N, 14.88; S, 51.09. Found: C, 31.74; H, 1.93; N, 14.69; S, 50.89.

Utilizing the procedure set forth above, but substituting the appropriate heterocyclic dithiocarbamate salt for triethylammonium 2-thiazolyldithiocarbamate, yields the compounds mentioned below:

| Example No. | Compound | m.p. ° C. |
|---|---|---|
| 62 | 2-(1,3,4-Thiadiazol-2-ylimino)-1,3-dithietane | 150–155 |
| 63 | 2-(2-Thienylimino)-1,3-dithietane | 89.5–90.5 |
| 64 | 2-(4-Methyl-2-thiazolylimino)-1,3-dithietane | 85–87 |
| 65 | 2-(5-Methyl-1,3,4-thiadiazol-2-ylimino)-1,3-dithietane | 147–148 |

EXAMPLES 66–77

Preparation of 2-(2-Ethoxyethyl)imino-1,3-dithietane

To a well-stirred mixture of 2,615 grams of 2-ethoxyethylamine in 9200 ml. of dimethylformamide in a water-cooled flask is added 739 grams of porous sodium hydroxide beads followed by 1,406 grams of carbon disulfide. When the sodium hydroxide has largely gone into solution (1 to 2 hours with temperature kept below 50° C. by cooling), the resulting mixture is added slowly to 6,440 grams of methylene bromide and 1,553 grams of sodium bicarbonate well stirred in 9,300 ml. of dimethylformamide. The addition time is about one hour with the reaction temperature kept below ca. 50° C. by external cooling. After an additional two hours at room temperature, the reaction mixture is poured into an equal volume of water and the organic material is partitioned into ethylene chloride. The ethylene chloride mixture is washed with water and with 5% hydrochloric acid and filtered free of some insoluble material. The ethylene chloride mixture is cooled to 10° C. to 15° C. and 2,310 ml. of 37% hydrochloric acid is added slowly with stirring. The resulting solids are collected by filtration, washed with ethylene chloride and methyl ethyl ketone, and air-dried to give the hydrochloric salt. The pulverized salt is stirred in water and 428 grams of 28% aqueous ammonia is added. The resulting product after recovery by extraction with ethylene chloride and solvent removal under vacuum is collected.

Purification by dry column chromatography on silica gel using chloroform as solvent gives the pure product as a pale yellow oil.

Anal.: Calc'd. for $C_6H_{11}NOS_2$: C, 40.65; H, 6.25; N, 7.90; S, 36.17. Found: C, 40.41; H, 6.36; N, 7.65; S, 36.05.

Following this procedure, but substituting the appropriate amine for 2-ethoxyethylamine, yields the compounds listed as follows:

| Example No. | Compound | m.p. °C. |
|---|---|---|
| 67 | 2-(Methylimino)-1,3-dithietane | — |
| 68 | 2-(Isopropylimino)-1,3-dithietane | — |
| 69 | 2-(tert-Butylimino)-1,3-dithietane | oil |
| 70 | 2-(Heptylimino)-1,3-dithietane | oil |
| 71 | 2-(Dodecylimino)-1,3-dithietane | 40.5–42 |
| 72 | 2-(Cyclohexylimino)-1,3-dithietane | 78–80 |
| 73 | 2-(Methylallylimino)-1,3-dithietane | oil |
| 74 | 2-(Isobutylimino)-1,3-dithietane | oil |
| 75 | 2-(1,4-Dimethylpentylimino)-1,3-dithietane | oil |
| 76 | 2-(n-Octylimino)-1,3-dithietane | oil |
| 77 | 2-(n-Hexylimino)-1,3-dithietane | oil |

EXAMPLE 78

Ovicidal and Larvicidal Activity against Insects and Ixodides Procedures

BUDWORM EGG AND LARVA TEST

Test solutions are prepared in 50% acetone/50% water, initially at 100 ppm. A one-inch square piece of cheesecloth, infested with about 100 eggs of *Heliothis virescens*, is dipped for a second in the solution along with a young cotton leaf. These are allowed to dry and are placed in a covered wax paper cup. Egg mortality ratings are made after three days. Larval mortality ratings are made after seven days. Ratings are as follows:

RATINGS:

+ = killed 86% to 100%
± = killed 41% to 85%
O = killed 0% to 40%
— = not tested Active compounds are further tested at tenfold dilutions until control is lost. The results obtained with test compound are reported below.

MOSQUITO EGG AND LARVA TEST

Test solutions are prepared in 50% acetone/50% water, initially at 1000 ppm. One ml. of 1000 ppm. solution is pipetted into 249 ml. of water in a 400 ml. beaker to yield a 4.0 ppm. test rate. About 100 eggs, 0 to 24 hours old, from *Anopheles quadrimaculatas* mosquitoes are added inside a wax paper ring floated on the surface of the water. Egg mortality results are noted after 2 days. Larval mortality results are noted after three days. Active compounds are further tested at tenfold dilutions until control is lost.

RATINGS:

+ = killed 86% to 100%
± = killed 41% to 85%
O = killed 0% to 40%
— = not tested The results of this test are reported below.

BOOPHILIS LARVA TEST

Effective control of acarina larvae is demonstrated in the following tests with larvae of *Boophilus microplus*, a one-host tick which can remain on a single host through its three life stages, i.e., larva, nymph and adult. In these tests, a 10% acetone/90% water mixture contains from 1.0 to 100 ppm. of test compound. Twenty larvae are enclosed in a pipet sealed at one end with a gauze material and solution containing the test compound is then drawn through the pipet with a vacuum hose simulating a spray system. The ticks are then held for 48 hours at room temperature and mortality is determined. The results achieved are set forth below. The rating system used is as follows:

| Mortality | Rating System Concentration | | Rating |
|---|---|---|---|
| >50% | at | 100 ppm. = | + |
| >50% | at | 33 ppm. = | ++ |
| >50% | at | 10 ppm. = | +++ |

TABLE I

Ovicidal and Larvicidal activity against insects and ixodid ticks with compounds of the structure:

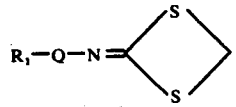

| Substituents | | Tobacco Budworm | | | | Mosquito | | | | Boophilus Larvae |
|---|---|---|---|---|---|---|---|---|---|---|
| | | Egg | | Larvae | | Egg | | Larvae | | |
| | | ppm. Concentration | | | | ppm. Concentration | | | | |
| $R_1$ | Q | 100 | 10 | 100 | 10 | 4.0 | 0.4 | 4.0 | 0.4 | |
| phenyl | —CH$_2$— | + | 0 | — | 0 | + | ± | — | + | . |
| 4-methylphenyl | —CH$_2$— | + | 0 | — | 0 | + | + | — | — | + |
| 4-chlorophenyl | —CH$_2$— | + | 0 | — | 0 | + | + | — | + | ++ |
| 2-chlorophenyl | —CH$_2$— | + | 0 | — | 0 | + | + | 0 | 0 | ++ |

TABLE I-continued

Ovicidal and Larvicidal activity against insects and ixodid ticks with compounds of the structure:

$$R_1-Q-N=\underset{S}{\overset{S}{\diamondsuit}}$$

| Substituents | | Tobacco Budworm | | | | Mosquito | | | | Boophilus |
|---|---|---|---|---|---|---|---|---|---|---|
| | | Egg | | Larvae | | Egg | | Larvae | | |
| | | ppm. Concentration | | | | ppm. Concentration | | | | |
| $R_1$ | Q | 100 | 10 | 100 | 10 | 4.0 | 0.4 | 4.0 | 0.4 | Larvae |
| 2-Cl-C₆H₄- | —CH₂— | + | 0 | — | 0 | + | + | — | — | ++ |
| 2,6-(CH₃)₂-C₆H₃- | —CH₂— | + | 0 | — | 0 | + | 0 | — | + | ++ |
| 2,3-Cl₂-C₆H₃- | —CH₂— | + | 0 | — | 0 | + | + | — | — | ++ |
| 2,4-Cl₂-C₆H₃- | —CH₂— | + | 0 | — | 0 | + | + | — | + | +++ |
| 1-naphthyl- | —CH₂— | ± | 0 | 0 | 0 | + | 0 | — | 0 | +++ |
| C₆H₅- | —CH(CH₃)— | + | 0 | — | 0 | 0 | 0 | + | 0 | |
| C₆H₅- | —CH₂—CH₂— | + | 0 | 0 | 0 | + | + | — | — | ++ |
| 2-furyl- | —CH₂— | + | 0 | — | 0 | + | 0 | — | 0 | |
| 2-thienyl- | —CH₂— | + | 0 | — | 0 | + | 0 | — | ± | |
| 2-pyrrolyl- | —CH₂— | 0 | | 0 | | 0 | 0 | ± | 0 | |

TABLE II

Ovicidal and larvicidal activity against insects and ixodid ticks with compounds of the structure:

$$R_2-A-W-N=\underset{S}{\overset{S}{\diamondsuit}} \text{ ; A=oxygen}$$

| Substituents | | Tobacco Budworm | | | | Mosquito | | | | Boophilus |
|---|---|---|---|---|---|---|---|---|---|---|
| | | Egg | | Larvae | | Egg | | Larvae | | |
| | | ppm. Concentration | | | | ppm. Concentration | | | | |
| $R_2-A$ | W | 100 | 10 | 100 | 10 | 4.0 | 0.4 | 4.0 | 0.4 | Larvae |
| C₂H₅O— | —CH₂CH₂— | 0 | | 0 | | ± | 0 | + | 0 | |
| Cl-C₆H₄-O— | —CH₂— | + | 0 | — | 0 | — | + | — | + | |
| C₆H₅-CH₂-O— | —CH₂— | + | 0 | + | 0 | — | 0 | — | ± | |
| C₂H₅OCH₂CH₂O— | —CH₂— | + | 0 | — | 0 | — | 0 | — | 0 | |
| cyclopentenyl-CH₂O— | —CH₂— | ± | | 0 | | — | 0 | — | 0 | ++ |

TABLE III

Ovicidal and larvicidal activity against insects and ixodid ticks with compounds of the structure:

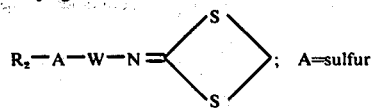  ; A=sulfur

| Substituents | | Tobacco Budworm | | | | Mosquito | | | | Boophilus |
| R₂A | W | Egg ppm. Concentration | | Larvae | | Egg ppm. Concentration | | Larvae | | Larvae |
| | | 100 | 10 | 100 | 10 | 4.0 | 0.4 | 4.0 | 0.4 | |
| $CH_3-S-$ | $CH_2$ | + | 0 | − | 0 | + | 0 | − | 0 | |
| $C_6H_5-S-$ | $CH_2$ | + | 0 | 0 | 0 | + | + | − | − | + |
| $Cl-C_6H_4-S-$ | $CH_2$ | + | 0 | − | 0 | − | + | − | − | |
| $Cl-C_6H_4-CH_2-S-$ | $CH_2$ | ± | | 0 | | − | 0 | − | 0 | |
| $CH_3O-\overset{O}{\underset{\|}{C}}-CH_2-S-$ | $CH_2$ | ± | | 0 | | − | 0 | − | 0 | |

TABLE IV

Ovicidal and larvicidal activity against insects and ixodid ticks with compounds of the structure:

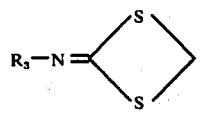

| Substituent | Tobacco Budworm | | | | Mosquito | | | | Boophilus |
| R₃ | Egg ppm. Concentration | | Larvae | | Egg ppm. Concentration | | Larvae | | Larvae |
| | 100 | 10 | 100 | 10 | 4.0 | 0.4 | 4.0 | 0.4 | |
| $CH_3-\overset{O}{\underset{\|}{C}}-$ | + | 0 | − | 0 | + | 0 | − | 0 | |
| $(CH_3)_2N-\overset{S}{\underset{\|}{C}}-$ | + | 0 | − | 0 | + | 0 | − | + | + |
| $C_2H_5O-\overset{O}{\underset{\|}{C}}-$ | + | ± | − | 0 | + | 0 | − | + | |
| $(C_2H_5)_2N-\overset{S}{\underset{\|}{C}}-$ | + | 0 | 0 | 0 | − | 0 | − | 0 | |
| $(CH_3)_2CH-O-\overset{O}{\underset{\|}{C}}-$ | + | + | − | 0 | + | 0 | − | 0 | |
| $(CH_3)_2N-\overset{O}{\underset{\|}{C}}-$ | + | 0 | − | 0 | − | 0 | − | 0 | |

TABLE V

Ovicidal and larvicidal activity against insects and ixodid ticks with compounds of the structure:

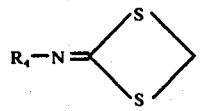

| Substituent | Tobacco Budworm | | | | Mosquito | | | | Boophilus |
| R₄ | Egg ppm. Concentration | | Larvae | | Egg ppm. Concentration | | Larvae | | Larvae |
| | 100 | 10 | 100 | 10 | 4.0 | 0.4 | 4.0 | 0.4 | |
| 2-pyridyl | + | 0 | − | 0 | + | 0 | − | 0 | |
| 3-pyridyl | + | 0 | − | 0 | + | 0 | − | 0 | |

TABLE V-continued

Ovicidal and larvicidal activity against insects and ixodid ticks with compounds of the structure:

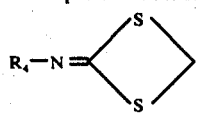

| Substituent R$_4$ | Tobacco Budworm | | | | Mosquito | | | | Boophilus Larvae |
|---|---|---|---|---|---|---|---|---|---|
| | Egg | | Larvae | | Egg | | Larvae | | |
| | ppm. Concentration | | | | ppm. Concentration | | | | |
| | 100 | 10 | 100 | 10 | 4.0 | 0.4 | 4.0 | 0.4 | |
| 4-pyridyl | + | 0 | − | 0 | + | 0 | − | 0 | |
| 4-Cl-pyridyl | + | 0 | − | 0 | + | 0 | − | 0 | |
| 4-CH$_3$-pyridyl | + | 0 | − | 0 | + | 0 | − | ± | + |
| 3-CH$_3$-pyridyl | ± | | 0 | | + | 0 | − | 0 | + |
| 6-CH$_3$-pyridyl | + | 0 | − | 0 | + | 0 | − | 0 | |
| 4,6-(CH$_3$)$_2$-pyridyl | + | 0 | − | 0 | + | 0 | − | 0 | + |
| 4-Br-pyridyl | + | 0 | 0 | 0 | − | 0 | − | + | |

TABLE VI

Ovicidal and larvicidal activity against insects and ixodid ticks with compounds of the structure:

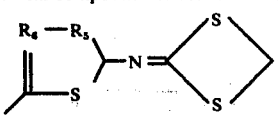

| Substituent R$_6$—R$_5$ / R$_8$ | Tobacco Budworm | | | | Mosquito | | | | Boophilus Larvae |
|---|---|---|---|---|---|---|---|---|---|
| | Egg | | Larvae | | Egg | | Larvae | | |
| | ppm. Concentration | | | | ppm. Concentration | | | | |
| | 100 | 10 | 100 | 10 | 4.0 | 0.4 | 4.0 | 0.4 | |
| thiazolyl | + | 0 | − | 0 | + | 0 | − | ± | + |

TABLE VI -continued

Ovicidal and larvicidal activity against insects and ixodid ticks with compounds of the structure:

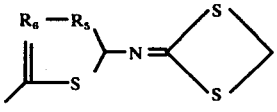

| Substituent $R_6-R_5 \atop R_8$ | Tobacco Budworm ppm. Concentration | | | | Mosquito ppm. Concentration | | | | Boophilus Larvae |
|---|---|---|---|---|---|---|---|---|---|
| | Egg | | Larvae | | Egg | | Larvae | | |
| | 100 | 10 | 100 | 10 | 4.0 | 0.4 | 4.0 | 0.4 | |
| 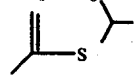 | + | 0 | − | 0 | + | 0 | − | 0 | |
| 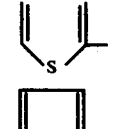 | + | 0 | − | 0 | + | 0 | − | 0 | + |
| 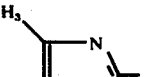 | + | 0 | − | | − | 0 | − | 0· | |
| 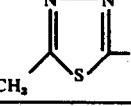 | + | 0 | − | 0 | +0 | − | 0 | | |

TABLE VII

Ovicidal and larvicidal activity against insects and ixodid ticks with compounds of the structure:

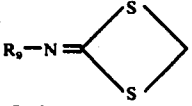

| Substituent $R_9$ | Tobacco Budworm ppm. Concentration | | | | Mosquito ppm. Concentration | | | | Boophilus Larvae |
|---|---|---|---|---|---|---|---|---|---|
| | Egg | | Larvae | | Egg | | Larvae | | |
| | 100 | 10 | 100 | 10 | 4.0 | 0.4 | 4.0 | 0.4 | |
| $CH_3-$ | 0 | | 0 | | 0 | 0 | + | 0 | |
| $i-C_3H_7-$ | 0 | | 0 | | 0 | | ± | | |
| $C_7H_{15}-$ | + | 0 | 0 | 0 | + | + | − | − | |
| 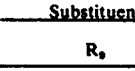 | 0 | | 0 | | ± | 0 | + | 0 | |
| 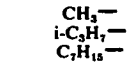 | 0 | | 0 | | + | + | − | − | + |
| 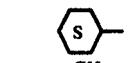 | 0 | | 0 | | + | | − | | |
| 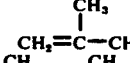 | | | | | | | | | |

EXAMPLE 79

OVICIDAL ACTIVITY OF SOUTHERN ARMYWORM EGGS, MEXICAN BEAN BEETLE EGGS AND SOUTHERN CORN ROOTWORM EGGS

Treatment of Southern Armyworm Eggs

In these tests, various concentrations of the test compound are prepared in a mixture of 65% acetone/35% water. The primary leaves of Sieva lima bean plants on which southern armyworm eggs were laid during the previous 24 hours were then dipped for about 5 seconds in the test solution. After the leaves were dry, they were placed in 9.0 cm. petri dishes containing moist filter paper on the bottom. The eggs were incubated at 80° F.

TREATMENT OF MEXICAN BEAN BEETLE EGGS AND TWO-SPOTTED SPIDER MITE EGGS

The procedure used in these tests is the same as described above for southern armyworm eggs.

TREATMENT OF SOUTHERN CORN ROOTWORM EGGS

Eggs were deposited on a 3 inch × 3 inch square of moist cotton that was placed in a cage with adults for two days. The eggs were removed from the cotton with deionized water and approximately 15 eggs were transferred to a 9.0 cm. filter paper by a medicine dropper. This filter paper was placed on top of two filter papers in a 9.0 cm. petri dish. All the papers were moist with deionized water. One ml. of the test solution was pipetted onto the eggs and filter paper. The solvent was allowed to evaporate before the lid was placed on the dish. The eggs were incubated at 80° F.

The data obtained in these tests are reported for test compounds as H = Hatch, P = Partial hatch, and N = No hatch.

S = non-resistant

TABLE VIII

Ovicidal Activity Against Insects and Acarina
Concentration in ppm.

| Compound Example Number | Southern Armyworm | | | Mexican Bean Beetle | | | Southern Corn Rootworm | | | Two-Spotted Spider Mites | | |
|---|---|---|---|---|---|---|---|---|---|---|---|---|
| | 300 | 100 | 30 | 300 | 100 | 30 | 300 | 100 | 30 | 300 | 100 | 30 |
| 2 | | H | H | N | N | H | N | N | N | N | P | H |
| 15 | N | H | H | N | H | H | N | N | H | H | H | H |
| 3 | N | H | H | N | H | H | | | | P | H | H |
| 4 | H | H | | P | H | H | | | | N | H | H |
| 5 | H | H | | N | H | H | | | | P | H | H |
| 1 | H | H | | N | H | H | | | | N | P | H |
| 7 | H | H | | N | H | H | | | | N | P | H |
| 14 | P | N | N | H | H | | | | | H | H | |
| 48 | N | H | H | N | P | H | | | | N | H | H |
| 47 | N | P | H | N | N | H | N | N | N | N | P | H |
| 50 | P | H | H | N | N | H | | | | P | H | H |
| 54 | N | N | H | N | H | H | | | | P | H | H |
| 60 | N | N | N | N | N | P | N | N | N | N | H | H |
| 59 | N | P | H | N | N | H | | | | H | H | H |
| 34 | N | H | H | N | N | H | N | N | N | H | H | |
| 37 | N | H | H | N | H | H | N | H | H | H | H | H |
| 70 | H | H | | N | H | H | N | N | H | H | H | |

EXAMPLE 80

SUPPRESSION OF FECUNDITY AND CHEMOSTERILANT EFFECT IN IXODIDES

Efficacy of the compounds of the present invention for suppression of fecundity in ticks is demonstrated in the following tests wherein engorged adult female *Boophilus microplus* ticks which have dropped from cattle are collected and used for testing.

Compound to be tested is dissolved in a 35% acetone/-65% water mixture in sufficient amount to provide from about 500 ppm. to 2000 ppm. of compound in the test solution. Ten ticks per treatment are used and they are immersed in test solution for three to five minutes, then removed and placed in cages and held at room temperature for three days. Counts of ticks laying eggs are then made and recorded. Eggs which were laid were placed in containers and kept for one month to observe hatching and determine chemosterilant effect. For these tests, non-resistant ticks as well as ethion-resistant and dioxathion-resistant ticks are used since the latter two are among the most difficult of their kind to control. Results of these tests are given in Tables IX and X below. The rating system used is as follows:

RATING SYSTEM

+ = > 50% did not lay eggs when treated at 2000 ppm.
++ = > 50% did not lay eggs when treated at 1000 ppm.
+++ = > 50% did not lay eggs when treated at 500 ppm.
O = more than 50% layed eggs when treated at 2000 ppm.
M = ethion-resistant ticks
D = dioxathion-resistant ticks

TABLE IX

Chemosterilant Effect of Iminodithietanes

| Compound Example Number | ppm. Compound | Number Ticks Treated | Number Ticks Producing Eggs | Number Sterile Egg Batches | Percent Sterile Egg Batches |
|---|---|---|---|---|---|
| 68 | 2000 | 30 | 27 | 10 | 37 |
| | 1000 | 30 | 30 | 5 | 17 |
| | 500 | 30 | 29 | 3 | 10 |
| | 0 | 60 | 0 | 0 | 0 |
| 3 | 2000 | 30 | 23 | 9 | 43 |
| | 0 | 60 | 51 | 9 | 17.5 |
| 4 | 2000 | 30 | 25 | 9 | 36 |
| | 1000 | 30 | 29 | 4 | 14 |
| | 0 | 60 | 51 | 9 | 17.5 |

TABLE X

Suppression of Fecundity in Ixodides

| Compound Example Number | Ticks | | |
|---|---|---|---|
| | M | D | S |
| 3 | + | + | ++ |
| 4 | 0 | + | 0 |
| 68 | 0 | + | 0 |

EXAMPLE 81

INTERFERENCE WITH NORMAL METAMORPHOSIS; JUVENILE HORMONE-LIKE EFFECT

Various concentrations of the test compound are prepared in a mixture of 65% acetone/35% water. Sieva lima bean leaves are dipped for 3 seconds in the test solution and the plant is placed in an exhaust hood to dry. A leaf is placed in a 9.0 cm. petri dish, which has a moist filter paper on the bottom, and ten last-instar Mexican bean beetle larvae. The larvae are at the stage where they feed for approximately 2 days. The dishes are covered and held at 80° F. for observations. Observations are made for abnormal effects such as adults unable to completely shed pupal skin, adults with deformed wings, adults unable to emerge, and the general pupal-adult appearance, and/or mortality on larvae, pupae, and adults. The results are set forth in Table XI below.

TABLE XI

| Compound | Concentration in ppm. 1000 | 100 |
|---|---|---|
| (CH₃)₂N—CS—N=⟨S-S⟩ | 40 to 80% deformed insects | insects appeared Normal |
| (C₂H₅)₂N—CS—N=⟨S-S⟩ | 40 to 80% deformed insects | insects appeared normal |
| Check (untreated insects) | appeared normal | |

These data indicate juvenile hormone-like effect for test compounds.

EXAMPLE 82

INHIBITION OF METAMORPHOSIS

A group of 25 larvae of the common malaria mosquito were transferred with a medicine dropper to a 50 ml. beaker containing 25 ml. of water. Test compound was formulated as an emulsion containing 0.1 gram of test material, 0.2 gram of Alrodyne 315 emulsifier, 10 ml. acetone and 90 ml. of water. This 1000 ppm. emulsion was diluted ten-fold with 65% acetone-35% water to give 100 ppm. One milliliter of the 100 ppm. emulsion was pipetted into 225 ml. of water in a 400 ml. beaker and stirred vigorously. The larvae in 25 ml. of water were added, giving a concentration of 0.4 ppm. The larvae were observed at 24 hours for mortality and retained an additional 5 days to observe for changes in metamorphosis from larva, to pupa, to adult. The larvae were fed a standard larval rearing diet during this observation period. The results are set forth in Table XII below.

TABLE XII

| Structure | Concentration of larval habitat was 0.4 ppm. |
|---|---|
| (CH₃)₂CH—N=⟨S-S⟩ | larvae pupated, but no adults emerged |

We claim:

1. A method for controlling insects and acarina comprising contacting the ova of said insects and acarina with an ovicidal amount of a compound having the formula:

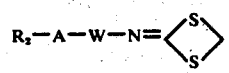

wherein W is selected from the group consisting of methylene, ethylene, lower alkyl ($C_1$-$C_5$) substituted methylene and lower alkyl ($C_1$-$C_5$) substituted ethylene; A is oxygen or sulfur; and $R_2$ is selected from the group consisting of $C_1$-$C_{12}$ alkyl, monocyclic alkyl ($C_3$-$C_{12}$) and bicyclic alkyl ($C_3$-$C_{12}$), phenyl, mono and diloweralkyl ($C_1$-$C_4$) phenyl, mono and dihalophenyl, furfuryl, tetrahydrofurfuryl, alkenyl of 2 to 8 carbon atoms, and lower alkoxy ($C_1$-$C_4$) lower alkyl ($C_2$-$C_3$).

2. A method for controlling insects and acarina by suppressing the fecundity thereof comprising applying to the habitat or dietary media of said insects and acarina a fecundity suppressing amount of a compound according to claim 1.

3. A method for controlling insects by applying a compound of claim 1 to the larvae, larval habitat or dietary media of said larvae in an amount effective to produce the juvenile hormone effect.

4. A method for controlling insects and acarina comprising applying to the larvae, larval habitat or dietary media of said larvae, a larvicidally effective amount of a compound according to claim 1.

5. A method for controlling ixodides comprising applying to adult female ixodid ticks a chemosterilizing amount of a compound according to claim 1.

6. The method according to claim 1 wherein the compound is 2-(2-ethoxyethylimino)-1,3-dithietane.

7. The method according to claim 1 wherein the compound is 2-(methoxymethylimino)-1,3-dithietane.

8. The method according to claim 1 wherein the compound is 2-(p-chlorophenoxymethylimino)-1,3-dithietane.

9. The method according to claim 1 wherein the compound is 2-(4-chloro-o-tolyloxymethylimino)-1,3-dithietane.

10. The method according to claim 1 wherein the compound is 2-(benzyloxymethylimino)-1,3-dithietane.

* * * * *